(12) United States Patent
Hanlon et al.

(10) Patent No.: US 9,155,832 B2
(45) Date of Patent: Oct. 13, 2015

(54) IRRIGATING CANNULA SYSTEM AND METHODS

(71) Applicant: Synergetics, Inc., O'Fallon, MO (US)

(72) Inventors: Matthew A. Hanlon, O'Fallon, MO (US); Matthew LaConte, Wildwood, MO (US)

(73) Assignee: Synergetics, Inc., O'Fallon, MO (US)

( * ) Notice: Subject to any disclaimer, the term of this patent is extended or adjusted under 35 U.S.C. 154(b) by 0 days.

(21) Appl. No.: 14/053,110

(22) Filed: Oct. 14, 2013

(65) Prior Publication Data

US 2014/0107625 A1    Apr. 17, 2014

Related U.S. Application Data

(60) Provisional application No. 61/713,227, filed on Oct. 12, 2012.

(51) Int. Cl.

| | | |
|---|---|---|
| *A61M 5/14* | (2006.01) | |
| *A61M 5/158* | (2006.01) | |
| *A61M 3/02* | (2006.01) | |
| *A61B 17/34* | (2006.01) | |
| *A61F 9/007* | (2006.01) | |
| *A61B 17/32* | (2006.01) | |
| *A61M 39/06* | (2006.01) | |

(52) U.S. Cl.
CPC .......... *A61M 5/1413* (2013.01); *A61B 17/3421* (2013.01); *A61F 9/00736* (2013.01); *A61M 3/0279* (2013.01); *A61M 5/158* (2013.01); *A61B 2017/320084* (2013.01); *A61B 2217/007* (2013.01); *A61F 9/007* (2013.01); *A61M 39/0606* (2013.01); *A61M 2039/0626* (2013.01); *A61M 2210/0612* (2013.01); *Y10T 29/49826* (2015.01)

(58) Field of Classification Search
CPC .............. A61M 5/158; A61M 3/0279–3/0295; A61M 5/1413; A61B 2017/32008; A61B 2217/007; A61B 2017/320084
USPC ................................................... 604/535, 539
See application file for complete search history.

(56) References Cited

U.S. PATENT DOCUMENTS

| | | | | |
|---|---|---|---|---|
| 4,014,333 | A | * | 3/1977 | McIntyre ........................ 604/43 |
| 4,551,129 | A | | 11/1985 | Coleman et al. |
| 4,573,979 | A | * | 3/1986 | Blake ............................ 604/240 |
| 4,897,079 | A | | 1/1990 | Zaleski et al. |
| 7,846,134 | B1 | * | 12/2010 | Nadolski et al. ......... 604/164.11 |
| 2008/0167604 | A1 | * | 7/2008 | Hong ............................. 604/27 |
| 2010/0190133 | A1 | * | 7/2010 | Martinez ........................ 433/81 |

OTHER PUBLICATIONS

International Search Report and Written Opinion of the International Searching Authority regarding PCT/US2013/064860 mailed on Jul. 23, 2014; pp. 14.

* cited by examiner

*Primary Examiner* — Nicholas Lucchesi
*Assistant Examiner* — Anh Bui
(74) *Attorney, Agent, or Firm* — Armstrong Teasdale LLP

(57) ABSTRACT

An irrigating cannula includes a hub having an inner passage and a side port extending through the hub and connecting to the inner passage. The inner passage is configured to receive an instrument, and a fluid passage is defined between the hub and the instrument. The fluid passage is configured to deliver a fluid through an incision in a body.

20 Claims, 10 Drawing Sheets

IRRIGATING CANNULA SYSTEM AND METHODS

CROSS REFERENCE TO RELATED APPLICATIONS

This application claims the benefit of U.S. Provisional Application No. 61/713,227, filed Oct. 12, 2012.

FIELD

This disclosure generally relates to cannula systems and, more specifically, to irrigating cannula systems and to related methods.

BACKGROUND

Cannula systems are used to keep an incision in a patient's body (e.g., in the eye) from closing after the incision tool (e.g., a trocar) is removed. Other surgical instruments may then be inserted through the cannula into the patient's body after removal of the trocar. Typical surgical procedures require a cannula for each surgical instrument inserted into the body. For example, a typical procedure requires one cannula for a surgical cutting instrument, another cannula for an illumination instrument, and yet another cannula for an irrigating instrument. Multiple cannulas increase surgical complexity, clutter the surgical field, and require multiple incisions that can increase pain, infection risk and recovery time. Accordingly, a cannula system that enables fewer incisions is needed.

This Background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

BRIEF SUMMARY

In one embodiment, an irrigating cannula is described. The irrigating cannula includes a hub having an inner passage and a side port extending through the hub and connecting to the inner passage. The inner passage is configured to receive an instrument, and a fluid passage is defined between the hub and the instrument, the fluid passage configured to deliver a fluid through an incision in a body.

In another embodiment, an irrigating cannula system is described. The system includes an irrigating cannula including a hub including an inner passage and a side port extending through the hub and connecting to the inner passage and a connection member coupled to the side port, the connection member configured to fluidly couple the inner passage and a fluid source. The irrigating cannula further includes a first cannula having a body and a tubular member extending therefrom, the first cannula coupled to the hub such that the tubular member extends through the inner passage to define a fluid passage between the hub and the tubular member. The first cannula is configured to receive an instrument and the fluid passage is configured to deliver a fluid around the first cannula. The system further includes a second cannula configured for insertion into a body, wherein the first cannula tubular member extends into the second cannula, and the fluid passage extends between the first cannula tubular member and the second cannula to provide irrigation to the body.

In yet another embodiment, a method of assembling an irrigating cannula is described. The method includes providing a hub having an inner passage and forming a side port extending through the hub and connecting to the inner passage. The inner passage is configured to receive an instrument, and a fluid passage is defined between the hub and the instrument, the fluid passage configured to deliver a fluid through an incision in a body.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

DETAILED DESCRIPTION

The disclosure generally relates to irrigating cannula systems that combine an instrument cannula with a practical, reliable, easy-to-use irrigation system, and to related methods. This single cannula system replaces traditional systems that require a dedicated cannula for irrigation. This system may be used in various surgical procedures such as pediatric ophthalmic procedures, and in particular, intra-ocular ophthalmic procedures for vitreo-retinal surgery. Thus, while reference is made herein to use of the system in ophthalmic procedures, it should be understood that the system can also be used in other surgical procedures.

Figure 1:
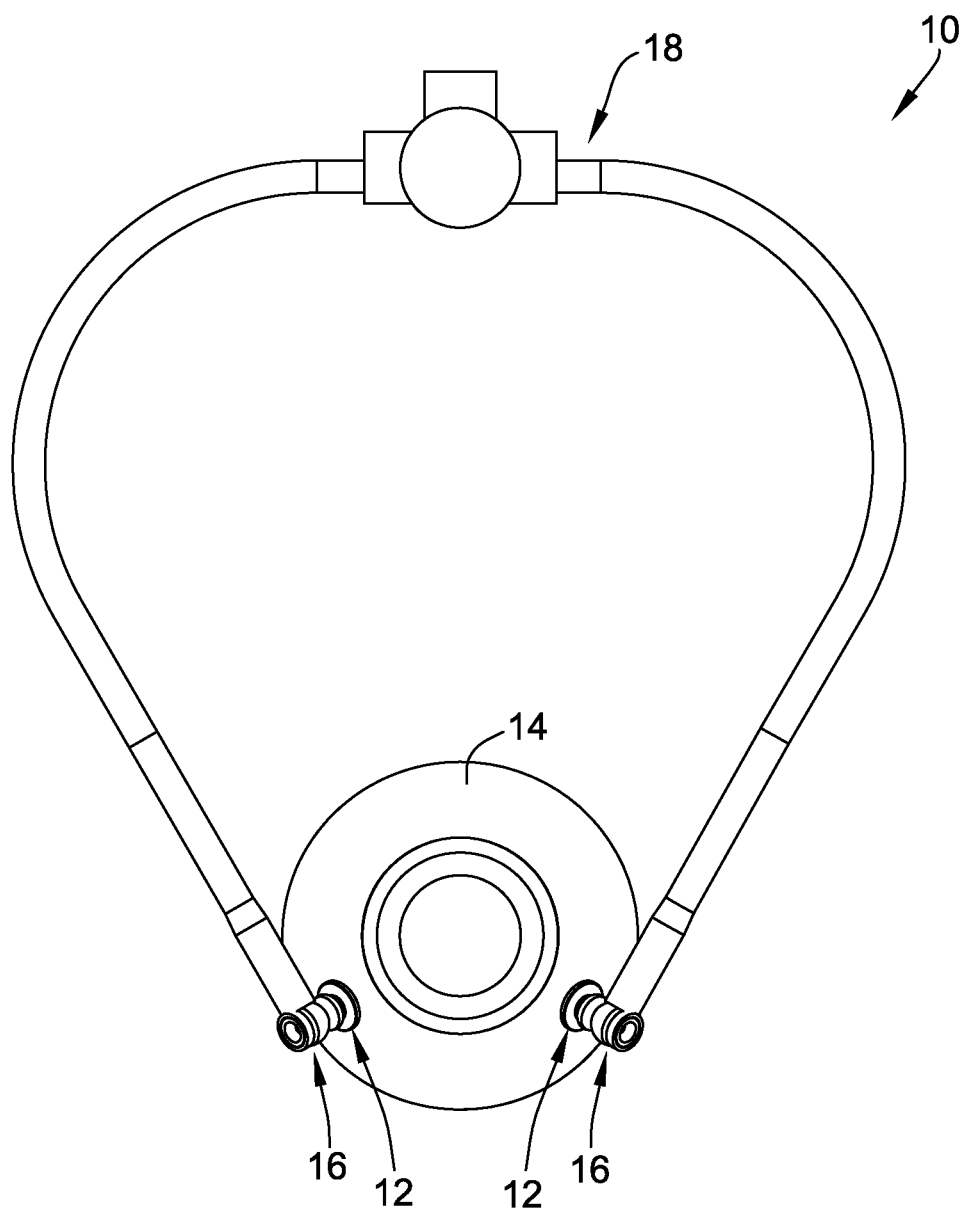
FIG. 1 is a perspective view of an irrigating cannula system of one embodiment.

Referring to FIG. 1, an irrigating cannula system of one embodiment is generally indicated by reference numeral 10. Irrigating cannula system 10 includes base cannulas 12 insertable into a body such as an eye 14 of a human body. An irrigating cannula 16 is coupled to each base cannula 12, and a fluid delivery system 18 is coupled to irrigating cannulas 16 to deliver an irrigation fluid to a region of eye 14 proximate base cannulas 12. At the same time irrigation is delivered to eye 14, a surgeon may insert a surgical instrument through the same device. Although described as separate components, base cannula 12, irrigating cannula 16 and/or fluid delivery system 18 may be formed as a single integral component. In the example embodiment, system 10 includes two base cannulas 12 and two irrigating cannulas 16 coupled to fluid delivery system 18. However, any number of complementary sets of base cannulas 12 and irrigating cannulas 16 may be coupled to fluid delivery system 18 (e.g., one, three, etc.).

Figure 2:
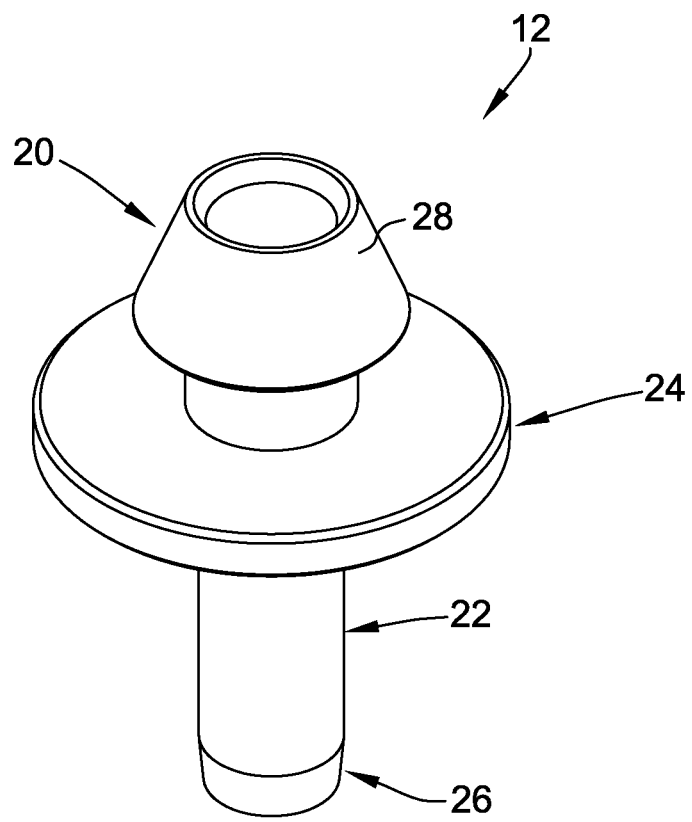
FIG. 2 is a perspective view of a cannula of the system shown in FIG. 1.

FIG. 2 illustrates exemplary base cannula 12 that is inserted into an incision formed in eye 14 such as by a trocar (not shown). Cannula 12 includes a body 20 and a tubular member 22. A shoulder portion 24 extends from tubular member 22 and rests against the surface of eye 14 to function as a stop to prevent cannula 12 from further insertion into the incision. Tubular member 22 includes a beveled portion 26 to improve insertion of cannula 12, and body 20 includes a flange 28 for coupling to irrigating cannula 16, as described further herein.

Figure 3:
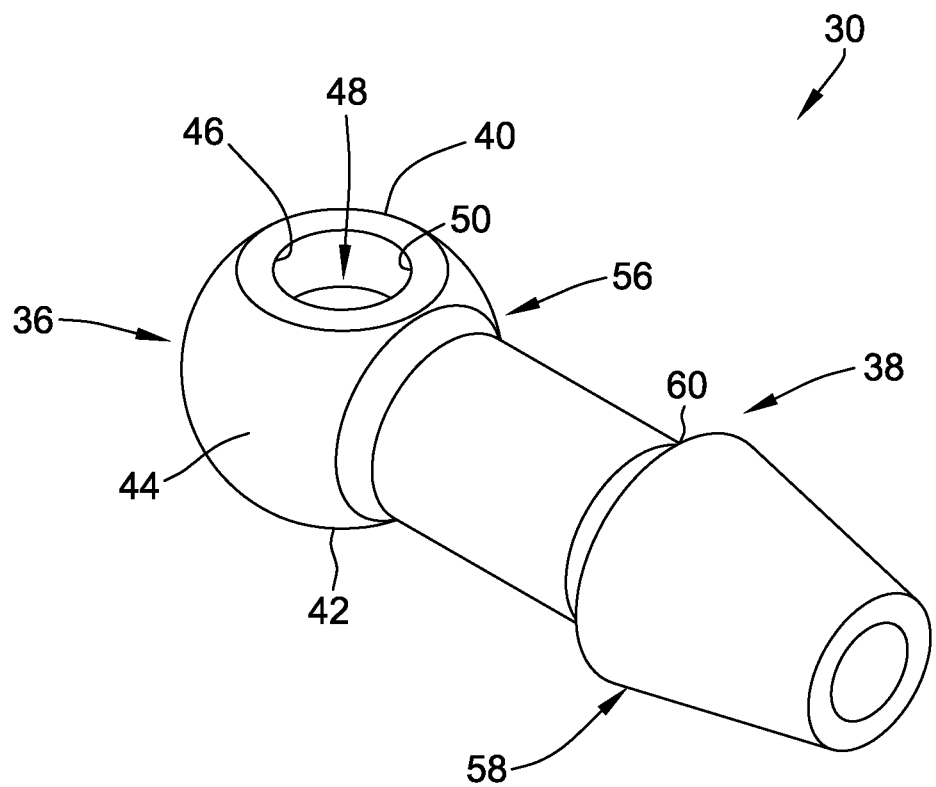
FIG. 3 is a perspective view of a fitting of the system shown in FIG. 1.

FIGS. 3-6 illustrate exemplary irrigating cannula 16 that includes a fitting 30, an internal cannula 32, and a sleeve 34. FIG. 3 illustrates fitting 30 that includes a hub 36 and a fluid connection member 38. In the example embodiment, hub 36 and fluid connection member 38 are integral. Alternatively, fluid connection member 38 may be a separate member coupled to hub 36. Hub 36 includes a first end 40, a second end 42, an outer wall 44 and an inner wall 46. Inner wall 46 defines an inner passage 48 through hub 36 and includes a first diameter portion 50 and a second diameter portion 52. In the example embodiment, inner passage 48 is substantially cylindrical. Alternatively, inner passage 48 may have any shape that enables irrigating cannula 16 to function as described herein.

In the example embodiment, a side port 54 (FIG. 6) is formed through hub 36 from outer wall 44 to inner wall 46 that connects to inner passage 48. Fluid connection member 38 is coupled to side port 54 and includes a first end 56 and a second end 58 having a flange 60. A fluid delivery line 62 is coupled to fluid connection member 38 and is retained by flange 60. As such, fluid connection member 38 fluidly couples fluid delivery line 62 (FIGS. 5 and 6) to inner passage 48 to facilitate delivery of a flow of irrigation fluid, as described further herein.

Figure 4:
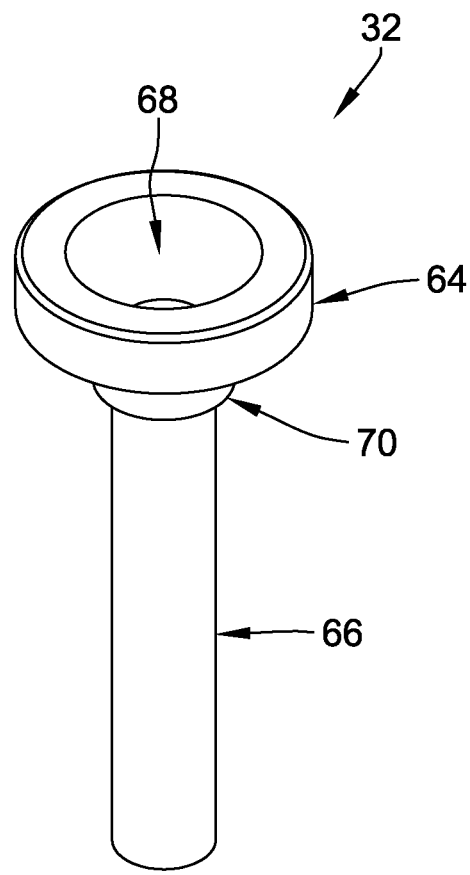
FIG. 4 is a perspective view of another cannula of the system shown in FIG. 1.
Figure 6:
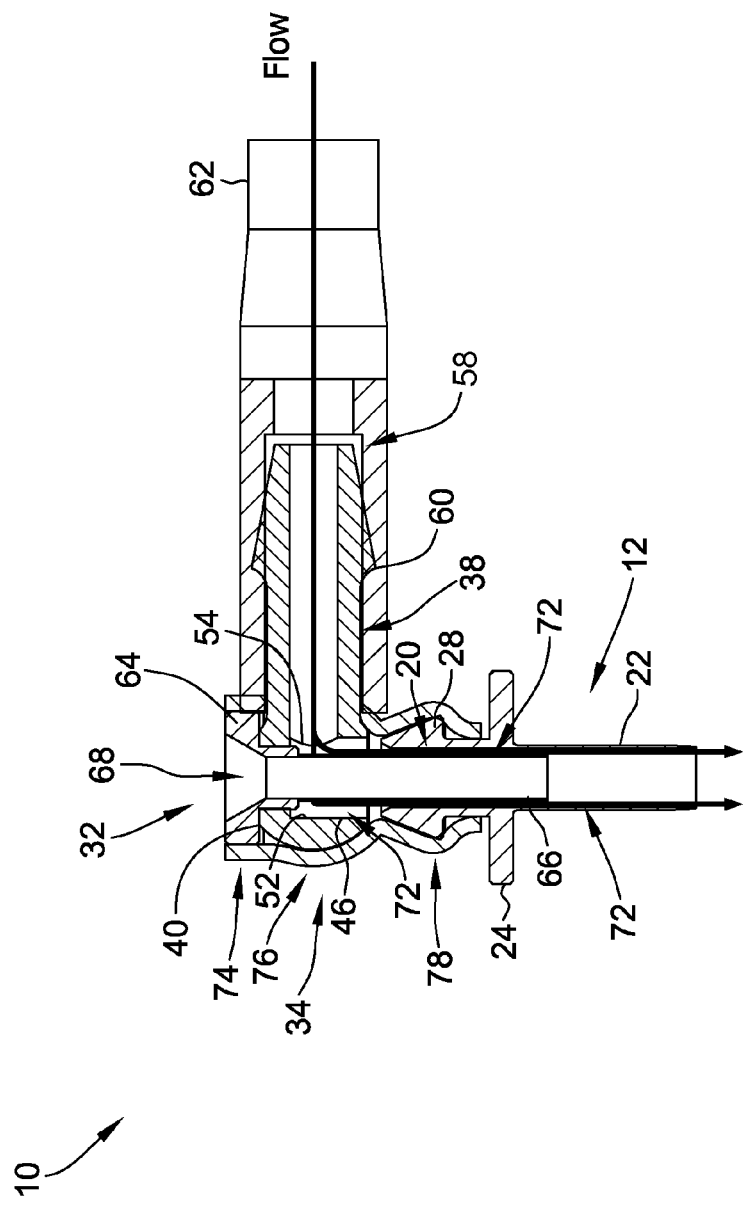
FIG. 6 is a cross-sectional view of the system shown in FIG. 5 and taken along line 6-6.

FIG. 4 illustrates exemplary internal cannula 32 of irrigating cannula 16. Internal cannula 32 includes a body 64 and a tubular member 66 defining an aperture 68 for receiving a surgical instrument (not shown). Body 64 includes a flanged portion 70, and cannula tubular member 66 is inserted within hub inner passage 48 such that body 64 rests against hub first end 40 and flanged portion 70 seats within first diameter portion 50 of hub 36. Alternatively, flanged portion 70 and/or tubular member 66 are sized and/or shaped to form a press-fit connection with hub 36. Once positioned within hub 36, cannula tubular member 66 defines a space or fluid passage 72 between hub inner wall 46 and the outer surface of tubular member 66 (FIG. 6). In this way, first diameter portion 50 acts as a restriction to fluid flow out of hub first end 40 when internal cannula 32 is positioned therein. Alternatively, cannula tubular member 66 may be omitted and fluid passage 72 is defined between hub inner wall 46 and an instrument inserted through aperture 68.

Figure 5:
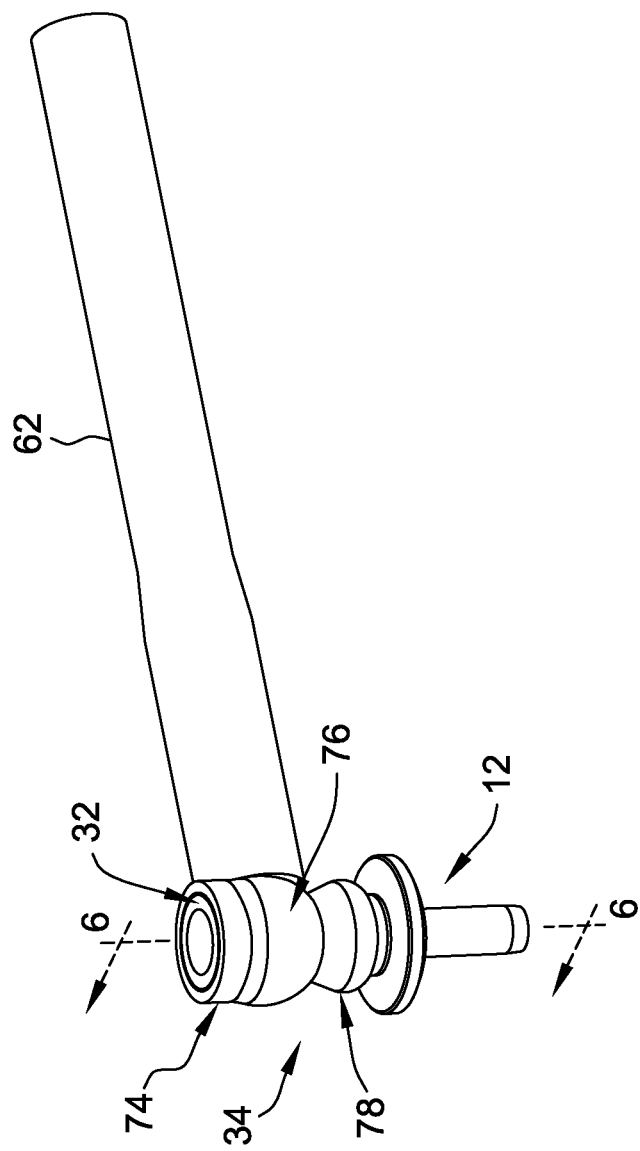
FIG. 5 is an enlarged perspective view of the system shown in FIG. 1.

FIG. 5 illustrates exemplary sleeve 34 that includes a first portion 74, a second portion 76, and a third portion 78. As illustrated in FIG. 6, sleeve first portion 74 fits firmly about internal cannula body 64, sleeve second portion 76 fits firmly about hub 36 and fluid connection member 38, and sleeve third portion 78 fits firmly around base cannula body 20 and corresponding flange 28. Sleeve third portion 78 is flanged, i.e., includes a flange, to facilitate attachment to flange 28 of base cannula 12. In some embodiments, sleeve first portion 74 is omitted from sleeve 34 (e.g., where internal cannula 32 is connected to hub 36 by a press-fit connection). In the example embodiment, sleeve 34 is fabricated from a flexible and resilient material (e.g. silicone) to facilitate a fluid tight seal between irrigating cannula 16 and base cannula 12, and between fitting 30 and internal cannula 32. Alternatively, sleeve 34 is fabricated from any material that enables irrigating cannula 16 to function as described herein.

FIG. 6 illustrates an exemplary assembled irrigating cannula system 10. Internal cannula 32 is inserted into hub 36 and fluid connection member 38 is coupled to hub side port 54. Sleeve 34 is positioned about internal cannula 32, hub 36 and fluid connection member 38, and base cannula 12. Fluid delivery line 62 is coupled to fluid connection member 38 to provide a flow of irrigation fluid to fluid passage 72. In the example embodiment, sleeve 34 and fluid delivery line 62 are separate members. Alternatively, sleeve 34 and fluid delivery line 62 may be formed as a single member. Irrigating cannula 16 is coupled to base cannula 12 such that cannula tubular member 66 is inserted into cannula tubular member 22, and sleeve 34 forms a fluid tight seal around base cannula body 20 and flange 28. As such, fluid passage 72 is formed between tubular member 66 and hub inner wall 46, sleeve 34, and the inner wall of tubular member 22 to facilitate fluid flow from fluid delivery line 62 out of tubular member 22. As such, when tubular member 22 is inserted into an incision, fluid flows out of tubular member 22 and through the incision. A surgical instrument may then be inserted through irrigating cannula 16 and base cannula 12 while at the same time an irrigation flow is directed to the incision, without the need for making two incisions in order to have both the instrument and fluid flow reach a surgical site.

As shown in FIG. 1, irrigation fluid is provided by fluid delivery system 18 to each fluid connection member 38 and into each fluid passage 72. The interconnections between each fitting 30, internal cannula 32, and sleeve 34 provide a tight fluid seal that facilitates preventing fluid leakage and that directs fluid out of the distal end of base cannula 12 through an incision. In the example embodiment, at least a portion of fluid passage 72 is sized to provide the desired volume of flow to the incision. For example, base cannula is a 20 ga size and internal cannula is a 23 ga size. Alternatively, base cannula is a 23 ga size and internal cannula is a 25 ga size. Alternatively still, base cannula is a 25 ga size and internal cannula is a 27 ga size. However, the cannulas may have any size that enables system 10 to function as described herein.

Figure 7:
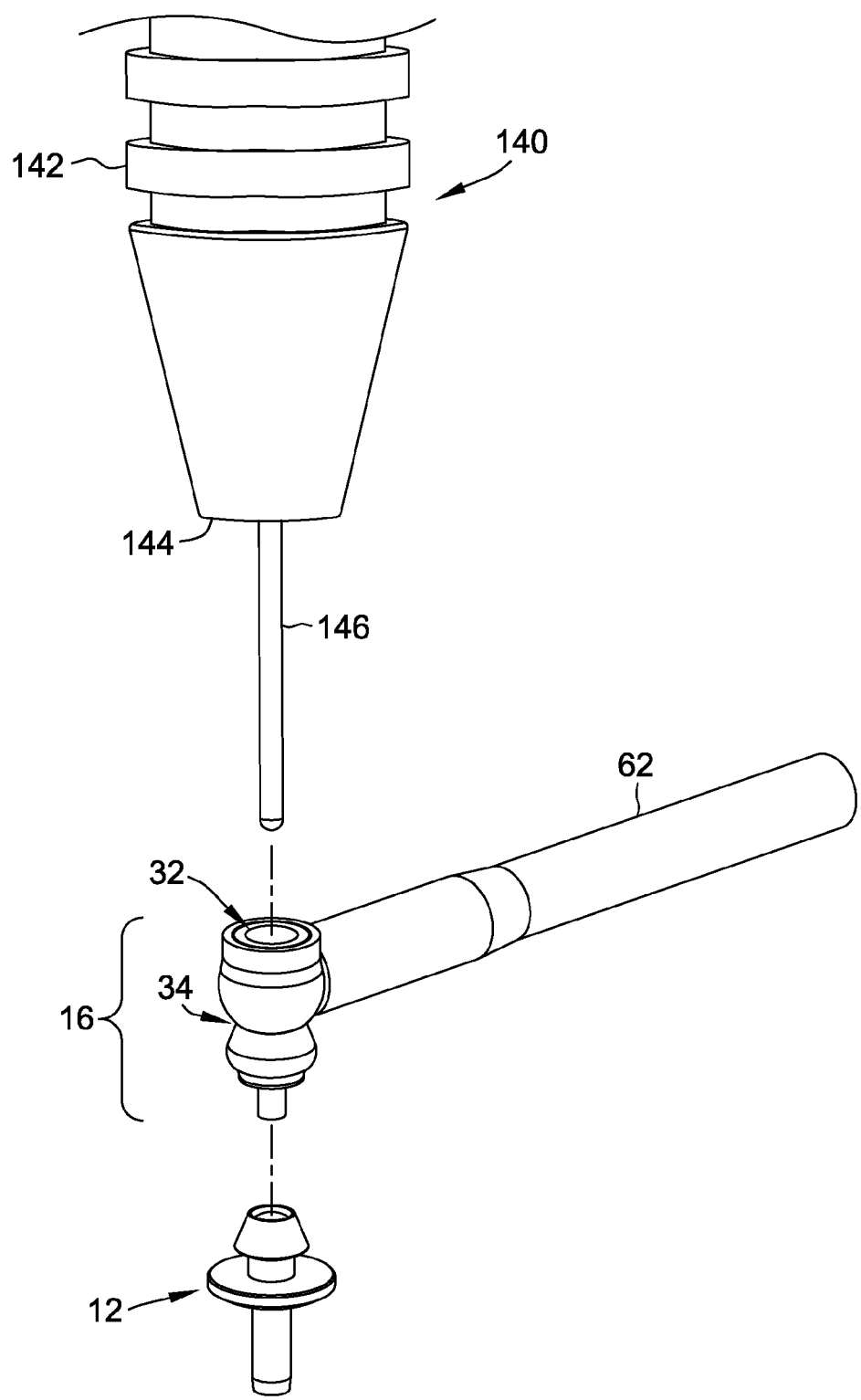
FIG. 7 is a partially exploded view of the irrigating cannula system shown in FIG. 5.

FIG. 7 is a partially exploded view of the assembled irrigating cannula system 10 shown in FIG. 6 and a blunt obturator 140 suitable for use in connecting irrigating cannula 16 to base cannula 12. Blunt obturator 140 includes a handle 142 having a first end 144, and a tip 146 connected to and extending longitudinally away from first end 144. Tip 146 is sized and shaped to be received within aperture 68 of internal cannula 32 to facilitate attachment of irrigating cannula 16 to base cannula 12. Alternatively, in embodiments where internal cannula 32 is omitted, tip 146 is sized and shaped to be received within inner passage 48 of hub 32 to facilitate attachment of hub 32 and/or sleeve 34 to base cannula 12.

In use, an incision is made in a human body (e.g. an eye) using an incision tool (e.g., a trocar). Tubular member 22 of base cannula 12 is inserted into the incision to prevent the incision from closing after the incision tool is removed. Irrigating cannula 16 is connected to base cannula 12 by inserting tubular member 66 into base cannula 12 and/or fitting sleeve 34 around base cannula 12, fitting 30, and/or internal cannula 32. An instrument (not shown in FIG. 6) is inserted into aperture 68 and through the incision during a surgical procedure. Irrigation fluid is fed through delivery line 62 and into inner passage 48 via fluid connection member 38. Irrigation fluid flows through the fluid passage 72, and through the incision. First diameter portion 50 of hub 36 and/or sleeve 34 maintains fluid flow towards the incision and prevents fluid from flowing out of first end 40 of hub 36. Alternatively, in embodiments where internal cannula 32 is connected to hub 36 by a press-fit connection, the press-fit connection between internal cannula 32 and hub 36 prevents fluid from flowing out of first end 40 of hub 36. In embodiments in which cannula tubular member 66 is omitted and fluid passage 72 is defined between hub inner wall 46 and an instrument inserted through aperture 68, described above, a plug (such as plug 106 shown and described with reference to FIGS. 8 and 9) may be inserted into inner passage 48 to maintain fluid flow to the incision when the instrument is removed.

Base cannula 12 may be attached to irrigating cannula 16 at the time tubular member 22 is inserted into the incision. Alternatively, irrigating cannula 16 is attached to base cannula 12 after tubular member 22 is inserted into the incision. In such embodiments, blunt obturator 140 may be used to align the irrigating cannula 16 with the base cannula 12, and facilitate attachment of hub 36 and/or internal cannula 32 to base cannula 12 (e.g., by fitting sleeve 34 over flange 28 of base cannula 12).

Figure 8:
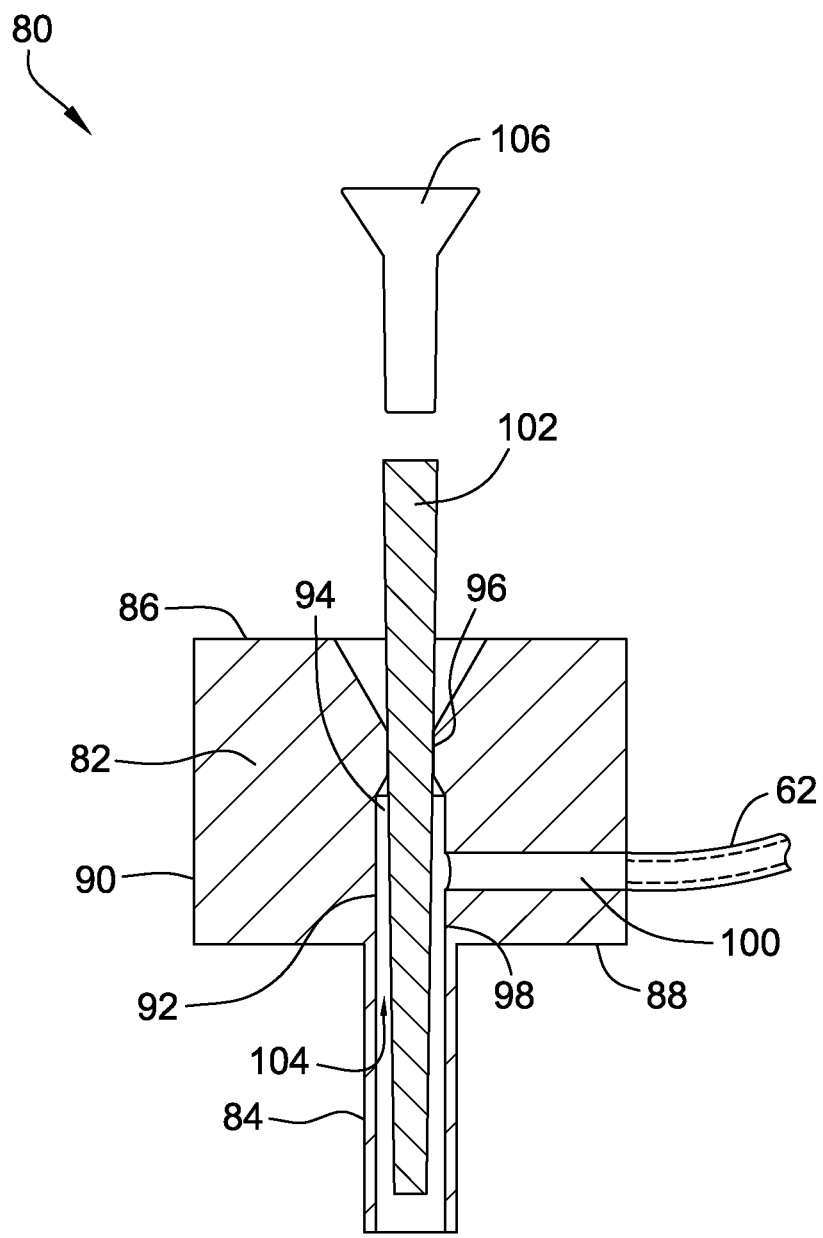
FIG. 8 is a cross-sectional view of an irrigating cannula system of another embodiment.

FIG. 8 illustrates another example irrigating cannula system 80 that includes a hub 82 and a tubular extension 84. Hub 82 includes a first end 86, a second end 88, an outer wall 90 and an inner wall 92. Inner wall 92 defines an inner passage 94 through hub 82 and includes a first diameter portion 96 and a second diameter portion 98. First diameter portion 96 facilitates restricting or inhibiting fluid flow toward hub first end 86 and directing fluid flow toward hub second end 88. In the example embodiment, inner passage 94 is substantially cylindrical. Alternatively, inner passage 94 may have any shape that enables system 80 to function as described herein. A side port 100 is formed through hub 82 from outer wall 90 to inner wall 92. A fluid delivery line 62 is coupled to side port 100 to fluidly couple delivery line 62 and inner passage 94.

In use, tubular extension 84 is inserted into an incision made in a human body (e.g. an eye). An instrument 102 is inserted into inner passage 94 and into the incision during a surgical procedure. As such, a fluid passage 104 is formed between hub inner wall 92 and instrument 102. Irrigation fluid flowing through delivery line 62 and side port 100 flows downward through fluid passage 104 (due at least in part to the flow restriction of first diameter portion 96) and flows through the incision. A plug 106 may be inserted into inner passage 94 to maintain fluid flow to the incision if instrument 102 is removed.

Figure 9:
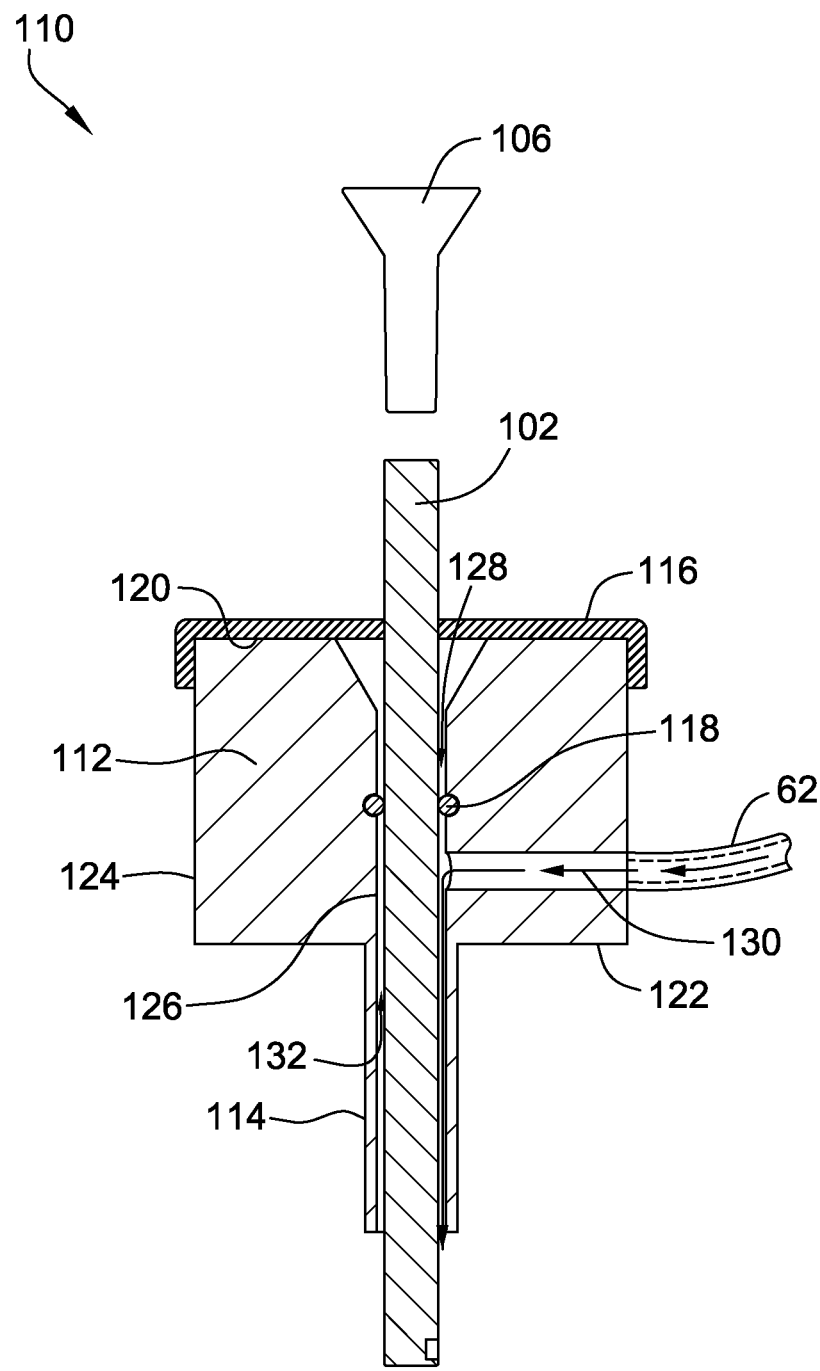
FIG. 9 is a cross-sectional view of an irrigating cannula system of another embodiment.

FIG. 9 illustrates another example irrigating cannula system 110 that includes a hub 112, a tubular extension 114, a valve cap 116 and a fluid restriction 118. Hub 112 includes a first end 120, a second end 122, an outer wall 124 and an inner wall 126. Inner wall 126 defines an inner passage 128 through hub 112, and fluid restriction 118 (e.g. an o-ring) is positioned within inner passage 128 to facilitate restricting fluid flow toward hub first end 120 and directing fluid flow toward hub second end 122. In the example embodiment, inner passage 128 is substantially cylindrical. Alternatively, inner passage 128 may have any shape that enables system 110 to function as described herein. A side port 130 is formed through hub 112 from outer wall 124 to inner wall 126. A fluid delivery line 62 is coupled to side port 130 to fluidly couple delivery line 62 and inner passage 128. Valve cap 116 is coupled to hub first end 120 to facilitate restricting fluid flow out of first end 120. Valve cap 116 may be the only such restriction in an embodiment where fluid restriction 118 is not present, and valve cap 116 may be any valve cap well known in the art.

In use, tubular extension 114 is inserted into an incision made in a human body (e.g. an eye). An instrument 102 is inserted into inner passage 128 and through the incision during a surgical procedure. As such, a fluid passage 132 is formed between hub inner wall 126 and instrument 102. Irrigation fluid flowing through delivery line 62 and side port 130 flows downward through fluid passage 132 (due at least in part to fluid restriction 118 and/or valve cap 116) and flows into the incision. A plug 106 may be inserted into inner passage 128 to maintain fluid flow through the incision if instrument 102 is removed.

Figure 10:
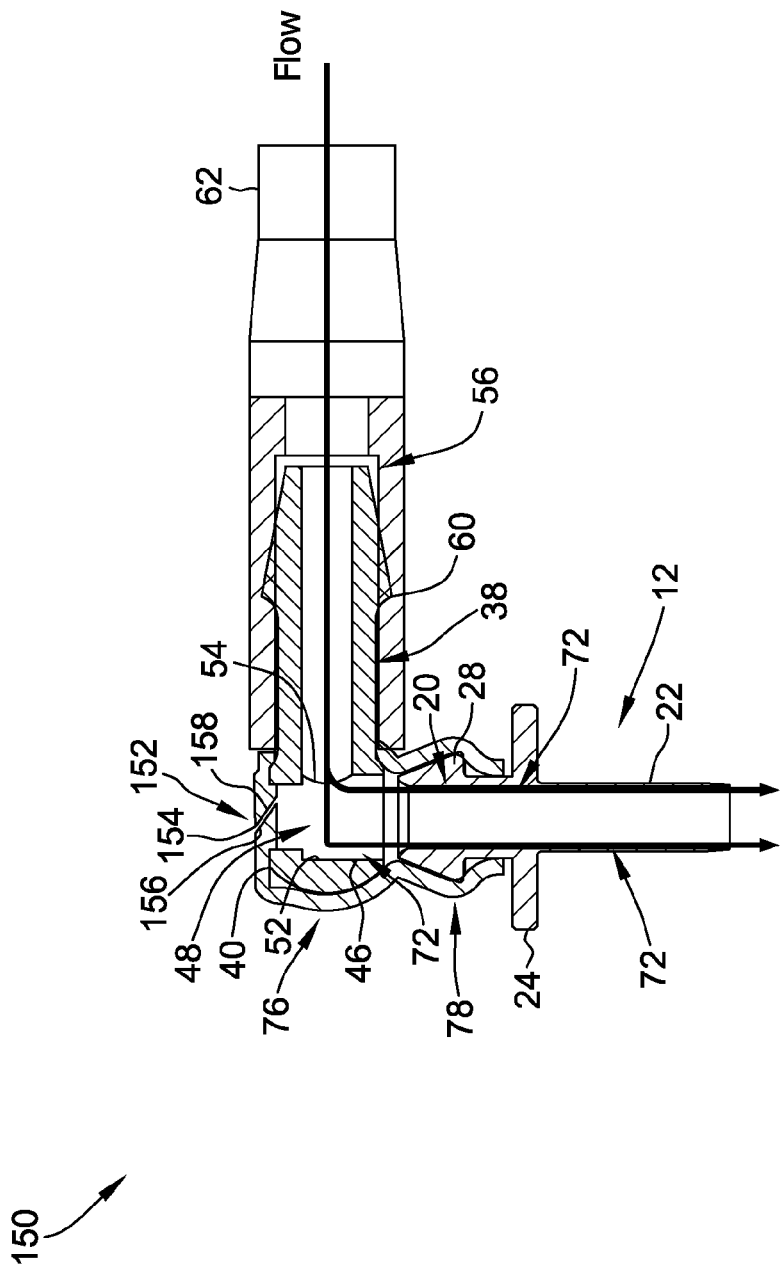
FIG. 10 is a cross-sectional view of an irrigating cannula system of another embodiment.

FIG. 10 illustrates another example irrigating cannula system 150. Irrigating cannula system 150 is essentially similar to the irrigating cannula system 10 illustrated in FIG. 6 and, as such, similar components are labeled with similar references. More specifically, internal cannula 32 is omitted from irrigating cannula system 150, and irrigating cannula system 150 includes a valve 152.

Valve 152 is configured to form a seal at first end 40 of hub 36 to prevent leakage of irrigation fluid. Further, valve 152 is configured to receive surgical instruments through an opening 154 therein, and sealingly engage surgical instruments inserted through opening 154. Valve 152 is fabricated from a flexible and resilient material (e.g. silicone) to facilitate a fluid tight seal between valve 152 and surgical instruments inserted through valve 152. In the illustrated embodiment, valve 152 is integrally formed with sleeve 34, although it is contemplated that valve 152 may be formed separately from sleeve 34.

Opening 154 is defined by angled walls 156 and 158 of valve 152, and is thus obliquely angled with respect to the direction of irrigation fluid flow. As a result, pressure exerted upon valve 152 by irrigation fluid causes opening 154 to close, thereby facilitating formation of a seal along first end 40 of hub 36. Alternatively, opening 154 may have any suitable configuration that enables valve 152 to function as described herein. While the illustrated valve 152 is described as being suitable for receiving surgical instruments, valve 152 may be configured to receive and sealingly engage other objects used with cannula systems, such as illumination devices (e.g., fiber optic cables).

In use, an incision is made in a human body (e.g. an eye) using an incision tool (e.g., a trocar). Tubular member 22 of base cannula 12 is inserted into the incision to prevent the incision from closing after the incision tool is removed. An instrument (not shown in FIG. 10) is inserted through valve 152, into inner passage 48 of hub 36, and into the incision during a surgical procedure. Irrigation fluid is fed through delivery line 62 and into inner passage 48 via fluid connection member 38. Irrigation fluid flows through the fluid passage 72, and into the incision. The sealing engagement between valve 152 and the instrument maintains fluid flow towards the incision and inhibits or completely prevents fluid from flowing out of first end 40 of hub 36. When the instrument is removed from inner passage 48, valve 152 returns to its initial configuration and seals first end 40 of hub 36. As such, a plug (such as plug 106 shown and described with reference to FIGS. 8 and 9) is not needed to seal first end 40 of hub 36 and maintain fluid flow.

Irrigating cannula systems according to embodiments of this disclosure provide dual surgical function within a single incision. In the specific embodiments described above, the system enables a surgical instrument to be inserted through cannulas, while an irrigation flow is directed about the instrument through an incision. The system requires only a single incision, as opposed to traditional systems that require a first incision for the irrigation flow and a second incision for a surgical instrument. As such, the irrigating cannula systems described herein provide a simple and elegant dual function system that is easy to use and reduces patient discomfort, infection risk and recovery time.

The systems described herein are well-suited for vitreoretinal procedures such as those associated with pediatric patients where the eye anatomy is small, or those associated with pediatric or adult patients having severe retinal detachments. In such procedures, state of the art surgical protocol often has inadequate access to allow use of a typical three-incision, three-cannula system. In contrast, the systems described herein provide dual surgical function with a single incision such that only a two-incision, two-cannula system is needed for the procedures.

Moreover, some known procedures require large instrumentation (e.g. 20 gauge). Accordingly, the instrumentation necessitates wound suturing at the completion of the surgical procedure, resulting in additional patient discomfort and longer surgery times. Twenty gauge instrumentation is not optimal for pediatric use and the additional complexity of providing irrigation to such an instrument restricts instrumentation options. The systems described herein combine the fluid delivery function of an irrigating cannula with an access cannula system that is scalable to 23 and smaller gauge surgery applications. The smaller surgery applications typically do not require post-surgical suturing and enable the use of non-irrigating, handheld instrumentation commercially available for non-irrigating cannula systems.

When introducing elements of the present invention or the embodiments thereof, the articles "a", "an", "the" and "said" are intended to mean that there are one or more of the elements. The terms "comprising", "including" and "having" are intended to be inclusive and mean that there may be additional elements other than the listed elements. The use of terms indicating a particular orientation (e.g., "top", "bottom", "side", etc.) is for convenience of description and does not require any particular orientation of the item described.

As various changes could be made in the above constructions and methods without departing from the scope of the invention, it is intended that all matter contained in the above description and shown in the accompanying figures shall be interpreted as illustrative and not in a limiting sense.

What is claimed is:

1. An irrigating cannula comprising:
a hub comprising a first end, a second end, an inner passage, and a side port extending through the hub and connecting to the inner passage, wherein the inner passage is configured to receive an instrument;
a first cannula having a body and a tubular member extending therefrom, the first cannula coupled to the hub such that the tubular member extends through the inner passage to define a fluid passage between the hub and the tubular member, the fluid passage extending from the side port of the hub through the second end of the hub and configured to deliver a fluid through an incision in a body, wherein the first cannula is configured to receive the instrument and the fluid passage is configured to deliver the fluid around the first cannula; and
a sleeve coupled about the first end of the hub and the first cannula.

2. The irrigating cannula of claim 1, further comprising a fluid connection member coupled to the side port, the fluid connection member configured to fluidly couple the inner passage and a fluid source.

3. The irrigating cannula of claim 1, wherein the sleeve is fabricated from a flexible material.

4. The irrigating cannula of claim 1, wherein the sleeve includes a flanged portion configured to couple to a second cannula such that the first cannula tubular member extends into the second cannula.

5. The irrigating cannula of claim 2, further comprising a fluid delivery line coupled to the fluid connection member.

6. The irrigating cannula of claim 1, wherein the first cannula has a gauge size smaller than or equal to 23 gauge.

7. The irrigating cannula of claim 1, wherein the irrigating cannula is configured to provide access through the incision for the surgical instrument.

8. The irrigating cannula of claim 1, wherein the sleeve comprises a valve configured to receive and sealingly engage the instrument.

9. An irrigating cannula system comprising:
an irrigating cannula comprising:
a hub comprising an inner passage and a side port extending through the hub and connecting to the inner passage;
a connection member coupled to said side port, said connection member configured to fluidly couple said inner passage and a fluid source; and
a first cannula having a body and a tubular member extending therefrom, the first cannula coupled to the hub such that the tubular member extends through the inner passage to define a fluid passage between the hub and the tubular member, wherein the first cannula is configured to receive an instrument and the fluid passage is configured to deliver a fluid around the first cannula;
a second cannula including a tubular member configured for insertion into a body, wherein the first cannula tubular member extends into the second cannula such that the second cannula tubular member extends beyond the first cannula tubular member, and the fluid passage extends between the first cannula tubular member and the second cannula to provide irrigation to the body; and
a sleeve coupled to the hub, the first cannula, and at least a portion of the second cannula, the sleeve including a first portion engaging the body of the first cannula, a second portion engaging the hub, and a third portion engaging the second cannula.

10. The system of claim 9, wherein the hub comprises a fluid restriction within the inner passage, the fluid restriction configured to prevent fluid passage thereby.

11. The system of claim 9, further comprising a fluid delivery line coupled to the fluid connection member.

12. The system of claim 9, wherein the fluid connection member is oriented substantially perpendicular to the first cannula tubular member.

13. The system of claim 9, wherein the first cannula has a gauge size of 23 gauge and the second cannula has a gauge size of 20 gauge.

14. The system of claim 9, wherein the first cannula has a gauge size of 25 gauge and the second cannula has a gauge size of 23 gauge.

15. The system of claim 9, wherein the first cannula has a gauge size of 27 gauge and the second cannula has a gauge size of 25 gauge.

16. The system of claim 9, wherein the irrigating cannula system is configured to deliver a fluid to an incision in a body and provide access through the incision for the surgical instrument.

17. The system of claim 9, wherein the second cannula is spaced apart from the hub.

18. The system of claim 17, wherein the sleeve is coupled about the hub and at least a portion of the second cannula such that the sleeve at least partially defines the fluid passage.

19. The system of claim 9, wherein the tubular portion of the second cannula includes an inwardly beveled portion that facilitates insertion of the second cannula into an incision in a body.

20. The system of claim 9, wherein the second cannula includes a flanged portion, the third portion of the sleeve coupled to the flanged portion.

* * * * *